United States Patent [19]

Blade

[11] Patent Number: 5,180,737
[45] Date of Patent: Jan. 19, 1993

[54] PHENYL OR BICYCLO-ALKENYLFLUORO AMIDE PESTICIDES

[75] Inventor: Robert J. Blade, Berkhamsted, United Kingdom

[73] Assignee: Roussel Uclaf, Romainville, France

[21] Appl. No.: 364,082

[22] Filed: Jun. 8, 1989

[30] Foreign Application Priority Data

Jun. 9, 1988 [GB] United Kingdom ............... 8813678
Oct. 6, 1988 [GB] United Kingdom ............... 8823437

[51] Int. Cl.$^5$ ................... A01N 37/18; C07C 233/13; C07D 307/10
[52] U.S. Cl. .................... 514/463; 514/523; 514/617; 549/454; 554/35; 554/54; 554/67; 558/393; 564/161; 564/180
[58] Field of Search ............. 514/523, 617; 549/454; 558/393; 564/161, 180; 260/404; 554/35, 54.67

[56] References Cited

U.S. PATENT DOCUMENTS 4,855,086 8/1989 Black et al. ............... 514/617

FOREIGN PATENT DOCUMENTS 0111105 6/1984 European Pat. Off. ............ 514/617
0164187 12/1985 European Pat. Off. ............ 514/617
0269457 6/1988 European Pat. Off. ............ 514/617
0317188 5/1989 European Pat. Off. ............ 514/617

OTHER PUBLICATIONS

Blade, Chemical Abstracts vol. 104, 1976, Abs. 202329v.
Wellcome, Chemical Abstracts vol. 101, 1984, Abs. 210764.
Miyakado, et al. Chemical Abstracts vol. 106, 1986, Abstract 62876f.
Chemical Abstracts, vol. 113, 1990, p. 221, Abstract No. 3642g JP-A-0200749 Sumitomo Chemical Co. Ltd. May 1, 1990.

Primary Examiner—Robert T. Bond
Assistant Examiner—Edward C. Ward
Attorney, Agent, or Firm—Nixon & Vanderhye

[57] ABSTRACT

Compound of the formula (I):

$$Q^1Q(CR^2{=}CR^3)_a(CR^4{=}CF)(CR^5{=}CR^6)_bC({=}O)NHR^1 \quad (1)$$

or a salt thereof, wherein $Q^1$ is a phenyl ring or a fused bicyclic ring system containing 9 or 10 ring carbon atoms at least one ring being aromatic, or $Q^1$ is a dihalovinyl group; Q is an alkyl chain containing 1 to 12 carbon atoms and optionally containing one or two oxygen atoms and/or an unsaturated group —$CR^7{=}CR^8$—, or —$C{\equiv}C$—, wherein $R^7$ and $R^8$ are selected from hydrogen or halo; a is 0 or 1; b is 0 or 1; the sum of a and b is 0 or 1; $R^2$, $R^3$, $R^4$, $R^5$ and $R^6$ are the same or different, and are independently selected from hydrogen, halo and $C_{1-4}$ alkyl; $R^1$ is selected from hydrogen and $C_{1-6}$ hydrocarbyl optionally substituted by dioxalanyl, halo, cyano, trifluoromethyl, trifluoromethylthio or $C_{1-6}$ alkoxy are disclosed which have pesticidal activity. Pesticidal formulations containing the compounds of the formula (I), their use in the control of pests and methods for their preparation are also disclosed.

15 Claims, No Drawings

PHENYL OR BICYCLO-ALKENYLFLUORO AMIDE PESTICIDES

This invention relates to pesticidal compounds, processes for their preparation and intermediates, therefor, compositions containing them and to their use in the treatment of pests. More particularly, the present invention relates to lipid amide pesticides.

European patent publication 111105 discloses unsaturated amide compounds of the formula $AXY(CE=CE^1)_nCONE^3E^4$ as insecticides wherein A is an aromatic 5- or 6-membered carbocyclic or heterocyclic ring, X is an alkene or alkyne unit, Y is a hydrocarbyl chain, E and $E^1$ are inter alia halogen, and $E^3$, $E^4$ are hydrogen or alkyl groups. N-isobutyl-2-bromo-7-phenyl-2E-hepten-6-ynamide is disclosed but no biological activity is given.

European patent publication 0164187, discloses unsaturated amide compounds of the formula $A^1X^1(CE=CE^1)_nCONE^3E^4$ as pesticides wherein $A^1$ is optionally substituted benzyl, naphthylmethylene or a 5-membered heteroarylmethylene ring and $X^1$ is an ether, thioether, S(O), S(O)$_2$, or amino linkage. No examples of fluoro substituted compounds are provided.

European patent publication 269457 discloses amides of the formula $A^2X^1Y(CE=CE^1)_nCONE^3E^4$ wherein $A^2$ is a monocyclic heteroaromatic group but no examples of compounds having halo substituents on the alkene unit are provided.

It has now been suprisingly discovered that lipid amides having a fluorine substituted -eneamide group display unforeseen levels of pesticidal activity.

Accordingly, the present invention provides a compound of the formula (I):

$$Q^1Q(CR^2=CR^3)_a(CR^4=CF)(CR^5=CR^6)_bC(=O)NHR^1 \quad (I)$$

or a salt thereof, wherein $Q^1$ is a phenyl ring or a fused bicyclic ring system containing 9 or 10 ring carbon atoms at least one ring being aromatic, or $Q^1$ is a dihalovinyl group; Q is an alkyl chain containing 1 to 12 carbon atoms and optionally containing one or two oxygen atoms and/or an unsaturated group $-CR^7=CR^8-$, or $-C\equiv C-$, wherein $R^7$ and $R^8$ are selected from hydrogen or halo; a is 0 or 1; b is 0 or 1; the sum of a and b is 0 or 1; $R^2$, $R^3$, $R^4$, and $R^5$ and $R^6$ are the same or different, and are independently selected from hydrogen, halo and $C_{1-4}$ alkyl; $R^1$ is selected from hydrogen and $C_{1-6}$ hydrocarbyl optionally substituted by dioxalanyl, halo, cyano, trifluoromethyl, trifluoromethylthio or $C_{1-6}$ alkoxy.

A halo substituent may be fluoro, chloro, bromo or iodo.

Suitably $Q^1$ is a phenyl ring optionally fused to a 5- or 6-membered carbocyclic ring, which carbocyclic ring may be aromatic or non-aromatic.

Preferably $Q^1$ is selected from phenyl, indanyl, naphthyl and tetrahydronaphthyl.

Suitable substituents for the ring system $Q^1$ include halo, cyano, $C_{1-6}$ alkyl and $C_{1-6}$ alkoxy each optionally substituted by one or more halogen atoms or the substituent is a group $S(O)_mR^9$ wherein m is 0, 1 or 2 and $R^9$ is $C_{1-6}$ alkyl optionally substituted by halo. The $Q^1$ ring system normally contains up to three substituents and suitably one or two substituents each as halo or trifluoromethyl. The substitution of the $Q^1$ ring system depends on the nature of this ring system but it is often convenient for $Q^1$ to be unsubstituted.

The alkyl chain Q may be attached at any position of the $Q^1$ ring system.

When Q contains an oxygen atom, this is not normally at the end of the alkyl chain adjacent to the alkene group. Suitably Q contains 1 to 8 carbon atoms and, optionally, one oxygen atom. When Q contains one oxygen atom, this is conveniently towards or at the end of the alkyl chain adjacent to $Q^1$. When Q contains two oxygen atoms, these are not normally adjacent. Q is preferably a $CH_2O(CH_2)_6$, $CH_2$, $O(CH_2)_7$ or $O(CH_2)_9$ group, the oxygen atom being adjacent to $Q^1$.

Preferably the sum of a and b is 1. Preferably $R^2$, $R^3$ are hydrogen, $R^4$ and $R^5$ are chosen from hydrogen and methyl and $R^6$ is chosen from hydrogen and fluoro. Most preferably $R^5$ is methyl and $R^6$ is hydrogen.

Suitably $R^1$ is $C_{1-6}$ alkyl optionally substituted by dixalanyl or $R^1$ is $C_{2-5}$ alkenyl. Most suitably $R^1$ is a branched chain $C_{4-6}$ alkyl group, such as isobutyl, 1,2-dimethylpropyl, 1,1,2-trimethylpropyl, 2,2-dimethylpropyl, 1-methylpropyl or $R^1$ is 2-methyl-prop-2-enyl or 2-methyl-1,3-dioxalan-2-yl. Preferably $R^1$ is isobutyl or 2-methyl-prop-2-enyl, when $R^5$ and $R^4$ are methyl.

One preferred group of compounds of the present invention includes those of the formula (IA)

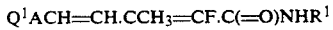

wherein $Q^1$, Q and $R^1$ are as hereinbefore defined.

A second preferred group of compounds of the present invention includes those of the formula (IB)

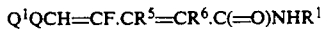

wherein $R^5$ is hydrogen or methyl, $R^6$ is hydrogen or fluoro and $Q^1$, Q and $R^1$ are as hereinbefore defined.

Preferred compounds include:
(2Z,4E)N-isobutyl-2-fluoro-3-methyl-11-(3,5-bistrifluoromethylbenzyloxy)undeca-2,4-dienamide
(2Z,4E)N-isobutyl-2-fluoro-3-methyl-6-(4-chloro-2-indanyl)hexa-2,4-dienamide.

Salts of the compounds of the present invention will normally be acid additions salts. Such salts may be formed from mineral or organic acids.

Preferred salts include those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methanesulphonic, ethanesulphonic, benzenesulphonic, toluene-p-sulphonic, lactobionic, glucuronic, thiocyanic, propionic, embonic, naphtheroic and perchloric acids.

The compounds of the formula (I) may exist in a number of stereoisomeric forms. The present invention encompasses both individual geometric and stereoisomers and mixtures thereof. The present invention also encompasses compounds of the formula (I), containing radioisotopes particularly those in which one to three hydrogen atoms are replaced by tritium or one or more carbon atoms are replaced by $^{14}C$.

In a further aspect, the present invention provides a process for the preparation of a compound of the formula (I) as hereinbefore defined which comprises:

a) the reaction of the corresponding acid or acid derivative $Q^1Q(CR^2=CR^3)_a(CR^4=CF)(CR^5=CR^6)_bCOZ$ with an amine $H_2NR^1$ wherein $Q, Q^1, R^2, R^3, R^4, R^5 R^6$, a, b and $R^1$ are as hereinbefore defined and Z is hydroxy, $C_{1-6}$ alkoxy, halo or a phosphoroimidate ester (—P(=O)(O-aryl)NH-aryl where aryl is $C_{6-10}$ aryl)

This reaction is normally carried out a non-extreme temperature, for example between −25° and 150° C. in an anhydrous aprotic solvent, such as ether, dichloromethane, toluene or benzene. The precise conditions will be dependent on the nature of the group Z, for example when Z is alkoxy the reaction is conveniently carried out at an elevated temperature, i.e. 50° to 125° C., and conveniently at reflux preferably in the presence of a trialkylaluminium compound, such as trimethylaluminium, which forms a complex with the amine $H_2NR^1$. When Z is halo or phosphoroimidate the reaction is conveniently carried out at 0° to 30° C. and suitably at room temperature preferably in the presence of a tertiary amine, such as triethylamine. If the acid derivative is an acid halide, for example the acid chloride, then it may be formed from the corresponding acid by reaction with a suitable reagent such as oxalyl chloride or thionyl chloride. When Z is a phosphoroimidate group then this is suitably formed from (PhO)P(=O)NHPhCl where Ph is phenyl. The acid, or the acid function in the compound $Q^1Q(CR^2=CR^3)_a(CR^4=CF)(CR^5=CR^6)_bCOZ$ may be prepared by hydrolysis of the corresponding ester. The esters may be prepared by a number of alternative routes, for example by a conventional Wittig or Wadsworth-Emmons reaction, using for example an aldehyde and an anion from a 2-fluoro-3-methyl phosphonocrotonate, in the presence of a base such as lithium diisopropylamide, butyllithium, sodium alkoxide or sodium hydride. This reagent may be produced for example by the following route or a modification thereof:

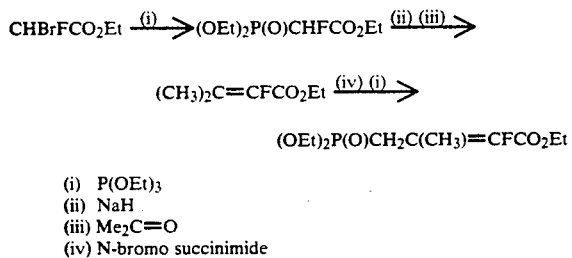

(i) $P(OEt)_3$
(ii) NaH
(iii) $Me_2C=O$
(iv) N-bromo succinimide

The above reaction scheme assists in illustrating the preparation of the intermediates and their conversion to compounds of the formula (I).

The esters may also be prepared by the reaction of an unsaturated aldehyde with a Reformatzky reagent derived from methyl dichlorofluoroacetate and zinc and subsequent reductive elimination as illustrated below:

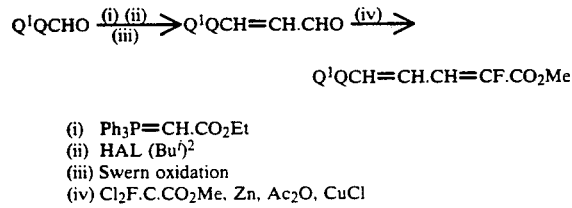

(i) $Ph_3P=CH.CO_2Et$
(ii) HAL $(Bu^i)^2$
(iii) Swern oxidation
(iv) $Cl_2F.C.CO_2Me$, Zn, $Ac_2O$, CuCl b) The reaction of an aldehyde or ketone $Q^1QCR^4=CF.CR^5(=O)$ with a compound $R^6CHR^{10}CONHR^1$ where $R^1, R^4, R^5, R^6, Q$ and $Q^1$ are as hereinbefore defined and $R^{10}$ is a group $(Z^2)_3P$ or $(Z^2)_2P(\rightarrow O)$ where $Z^2$ is alkyl, alkoxy (preferably ethoxy) or aryl (preferably phenyl).

This reaction is normally carried out a temperature between −70° and 0° C. in an anhydrous aprotic solvent such as tetrahydrofuran. The compound $R^6CHR^{10}CONHR^1$ is reacted initially with 2 equivalents of a base such as lithium diisopropylamide, butyllithium, sodium alkoxide or sodium hydride, the precise conditions are dependent on the nature of $Z^2$ and $Z^3$, prior to reaction with the compound $Q^1QCR^4=CF.CR^5(=O)$.

A compound of the formula $R^6CHR^{10}CONHR^1$ may be prepared for example by the following route or a modification thereof.

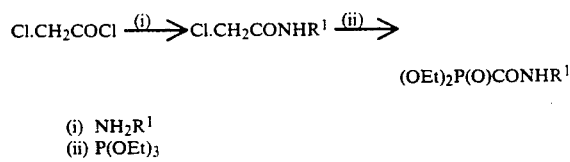

(i) $NH_2R^1$
(ii) $P(OEt)_3$

The aldehyde intermediates of the present invention form a further aspect of the present invention and may be prepared for example by the following route or a modification thereof.

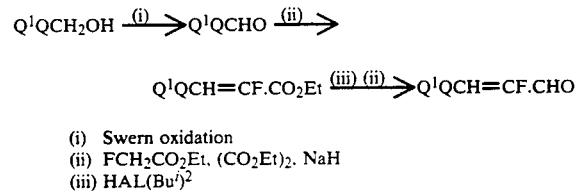

(i) Swern oxidation
(ii) $FCH_2CO_2Et$, $(CO_2Et)_2$, NaH
(iii) $HAL(Bu^i)^2$

The intermediates of the present invention form a further aspect of the present invention and may be prepared where appropriate by standard methods other than those described.

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustile solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant of surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders, and, if desired, granulating, compacting or encapsulating the products.

Sprays of a compound of Formula (I) may comprise a solution in an organic solvent, (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulfphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca Domestica*). In addition, certain compounds of formula (I) have activity against other arthropod pests including *Myzus persicae, Tetranychus urticase, Plutella xylostella,* Culex spp. *Tribolium castaneum, Sitophilus granarius, Periplaneta amiercana* and *Blattela germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorphoptrus, Meligethes, Hypothenemus, Hylesinus, Acalymma, Lema, Paylliodes, Leptinotarsa, Gonocephalum, Agriotes, Dermolepida, Heteronychus, Phaedon, Tribolium, Sitophilus, Diabrotica, Anthonums or Anthrenus spp.), Lepidoptera (e.g. Ephestia, Mamestra, Earias, Pectinophroa, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola (spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hydroderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococus, Helopeltis, Hygus, Dysdercus, Oxycarenus, Nezara, Aleurodes, Triatoma, Psylla, Mysus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopsis or Monomorium spp.), Isoptera (e.g. Odontotermes and Reticultitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*), Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notodnes, Sacroptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates and organophosphates), and/or with attractants, repellents, bacteriocides, fungicides, nematocides, anthelmintics and the like. Furthermore, it has been found htat the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

Industrial Applicability

Compounds of the present invention show activity as pesticides.

The following Examples illustrate, in a non-limiting manner, preferred aspects of the invention.

EXPERIMENTAL

General Synthetic Methods and Procedures

Various compounds were synthesized and characterized in accordance with the following experimental procedures.

$^1$H H.m.r. spectra were obtained on a Bruker AM-250 spectrometer in deuterochloroform solutions with tetramethylsilane as internal standard and are expressed as ppm from TMS, number of protons, number of peaks, coupling constant J Hz.

Progress of reactions could also be conveniently monitored on plastic sheets (40×80 mm) precoated with 0.25 mm layers of silica gel with fluorescent indicator and developed in appropriate solvent or solvent mixture. Temperatures are in degrees Celsius throughout.

Conventional work up was performed as follows;

The reaction mixture was partitioned between an organic solvent and water. The phases were separated and the organic phase washed with at least an equivalent volume of dilute aqueous acid or dilute aqueous base as appropriate, and then with a saturated brine wash. The organic phase was then dried over a drying agent, suitably magnesium sulphate, and filtered. The volatile solvents were removed and the resulting product subjected to the appropriate purification and used in the next stage of synthesis or analysed as the final product.

EXAMPLE 1

(2Z,4E) N-Isobutyl 2-fluoro-3-methyl-11-(3,5-bistrifluoromethylbenzyloxy) undeca-2,4-dienamide (i) Ethyl bromofluoroacetate (ex Fluorochem) (25 g) and triethyl phosphite (ex Aldrich) (29 g) were heated together at 140°-5° for 6 hours in a vessel equipped with a fractionating column. When all the ethyl bromide had distilled off the residue was distilled to give triethyl 2-fluoro-2-phosphonoacetate (22 g) (bp 98°-108° at 0.8 mm). The latter (20 g) was added dropwise to hexane washed sodium hydride (3.3 g of 60% dispersion) in dry ether (85 ml). After 3 hours at room temperature and 30 mins under reflux, acetone (6.1 ml) was added and the mixture stirred for 4 days at room temperature under nitrogen. After conventional work up the crude product was distilled to give ethyl 2-fluoro-3-methyl-but-2-enoate (4 g) (bp. 60°-2° at 15 mm). (Ref. Machledit & Wessendorf. *Ann.* 674, 1, (1964)).

Ethyl 2-fluoro-3-methyl-but-2-enoate (4 g, 27.4 mmol), N-bromosuccinimide (5.36 g, 30 mmol) ex Aldrich) and benzoyl peroxide (30 mg) were heated together under reflux in tetrachloromethane (60 ml) under illumination from a bright light. After 2 hours the solvent was removed and the residue taken up in hexane, filtered through "celite" and concentrated. Short path distillation gave a mixture of (E) and (Z) ethyl 4-bromo-2-fluoro-3-methylbut-2-entoates (4 g) which was heated under reflux in a Vigreux flask with triethylphosphite (3.82 g, 23.07 mmol) at 140°-150°. After 2 hours the crude product was purified by bulb to bulb distillation to give triethyl 2-fluoro-3-methyl-4-phosphonocrotonate (3.5 g, bp 160°-70° at 0.5 mm).

(ii) Sodium metal (1.7 g) was added to 1,7-heptandiol (19.8 g) in dry toluene (150 ml) at 100°. The whole was heated under reflux until all the sodium had been consumed and 3,5-bistrifluoromethyl benzyl bromide (ex Aldrich) (23.0 g) in dry toluene (50 ml) was added. After heating under reflux for circa 5 hours the reaction mixture was worked up in conventional fashion and the crude product purified by column chromatography on silica (ether/hexane) to give 7-(3,5-bistrifluoromethyl-benzyloxy)heptan-1-ol.

The above alcohol (1 g) was oxidised under Swern conditions (dimethyl sulphoxide (450 mg), oxalyl chloride (248 μl), triethylamine (1.58 ml)) in dichloromethane (25 ml) to give 7-(3,5-bistrifluoromethylbenzyloxy)-heptan-1al. This was used directly in the next stage.

(iii) A solution of lithium diisopropylamide in dry tetrahydrofuran, prepared from diisopropylamine (408 μl) and n-butyl lithium (1.74 ml at 1.6M), was treated at −60° with triethyl 2-fluoro-3-methyl-4-phosphonocrotonate (949 mg) in tetrahydrofuran under nitrogen. The temperature was allowed to reach −10° and then recooled to −40° whereupon the above aldehyde was added. The reaction was maintained at 5° for 16 hours and worked up in conventional fashion. Chromatography on silica (4:1 hexane:ether) gave (2Z, 4E) ethyl 2-fluoro-3-methyl-11-(3,5-bistrifluoromethylbenzyloxy)undeca-2,4-dienoate.

(iv) The above ester (0.4 g) in dry toluene (2.5 ml) was added at −10° to a complex prepared from trimethylaluminium in toluene (498 μl) at 2M) and redistilled isobutylamine (108 μl) in toluene (3.5 ml). After heating under reflux for 5 hours the reaction mixture was allowed to cool, treated with 2N hydrochloric acid and stirred for 30 mins. Dilution with ether and conventional work up gave a crude product which was purified by flash column chromatography on silica (1:1 ether:hexane) to give the title compound as a pale yellow oil (0.39 mg).

EXAMPLE 2

(2Z,4E) N-Isobutyl 2-fluoro-3-methyl-6-(4-chloro-2-indanyl)hexa-2,4-dienamide

2-Chlorocinnamic acid (26 g) (ex Aldrich) in glacial acetic acid (250 ml) was subjected to hydrogenation at 45 psi in the presence of 10% palladium/charcoal. Conventional work-up gave 3-(2-chlorophenyl)propanoic acid (26.3 g) which was added to polyphosphoric acid (220 g) at 80° under nitrogen. After stirring for 2 hours at 80° the mixture was allowed to cool and added to water, ether extraction and conventional work up gave 4-chloroindan-1-one as a brown solid (10 g).

A solution of the above indanone (10 g) in dry benzene (100 ml) was warmed to 80°, with allyl alcohol (7.66 g), 2,2-dimethyoxypropane (8.1 ml) and 4-toluene sulphonic acid (50 mg), in a distillation apparatus. The temperature was raised to 120° and the volatiles distilled off. The residue was purified by column chromatography (silica; 9:1, hexane:ether) to give 2-allyl-4-chloroindan-1-one (3.1 g).

Amalgamated zinc (prepared from zinc powder (6 g), mercuric chloride (0.6 g)) was heated under reflux for 7 hours with 2-allyl-4-chloro-indan-1-one (3 g), toluene (20 ml), conc. hydrochloric acid (20 ml), water (8 ml) and acetic acid (2 ml). Upon cooling conventional work-up gave a crude product which was purified by chromatography (silica/hexane) to give a 2-allyl-4-chloroindane (1.8 g). 2-Allyl-4-chloroindane (0.8 g) in dry methanol (10 ml) and dry dichloromethane (2 ml) was reacted at −35° with ozone until the blue colour persisted. After purging with nitrogen the solution was stirred 16 hours with dimethyl sulphide (2.58 g). The volatiles were removed and the residue taken up in tetrahydrofuran (10 ml) and heated under reflux with 4-toluenesulphonic acid (30 mg) and water (circa 0.5 ml) for 2 hours. After conventional work up the product, 2-(4-chloro-2-indanyl) ethanol, was obtained as a yellow oil (0.8 g).

The above aldehyde was converted by analogy with example 1 to give the final compound.

EXAMPLE 3

(2Z,4E)N-Isobutyl 2-fluoro-3-methyl-12-(2-naphthyloxy)dodeca-2,4-dienamide

Prepared by analogy with example 1 except that 8-(2-naphthyloxy) octan-1-al, prepared according to EP 251-472 was used in step (iii).

EXAMPLE 4

(2Z,4E)N-Isobutyl 2-fluoro-3-methyl-12-(3,5-bistrifluoromethylphenoxy) dodeca-2,4-dienamide 3,5-Bistrifluoromethylphenol (ex. Aldrich) was reacted first with sodium hydride and then with 8-bromooctan-1-ol (ex. Aldrich) in anhydrous dimethyl formamide, by analogy with example 6, to give 8-(3,5-bistrifluoromethylphenoxy)-octan-1-ol. The latter was converted to the title compound by analogy with example 1.

EXAMPLE 5

(2Z,4E)N-Isobutyl 2-fluoro-3-methyl-12-(3,4-dichlorophenoxy) dodeca-2,4-dienamide Prepared by analogy with example 4 except that 3,4-dichlorophenol (ex. Lancaster) was used in the first stage.

EXAMPLE 6

(2Z,4E)N-Isobutyl 2-fluoro-3-methyl-6-(5-bromoindan-2-yl) hexa-2,4-dienamide 4-(3-Chloropropanoyl)bromobenzene (ex. Lancaster) (24.7 g) added to aluminium chloride (100 g) and sodium chloride (25 g) at 180°. After 30 minutes at 180°-220° the mixture was poured onto ice and treated with acetic acid (30 ml). The resultant product was collected and taken up in ether, the organic solution was dried and concentrated and the residue recrystallised from methanol to give 5-bromoindan-1-one (9 g).

A solution of the above (6.3 g) in dry diethyl ether (400 ml) treated at 0° with bromine (4.78 g). The mixture was washed with water and worked up in standard fashion to give 2,5-dibromoindan-1-one (7.5 g).

The sodium salt of diethyl malonate was prepared in toleune from sodium (0.71 g) and diethyl malonate (6.2 g). 2,5-Dibromoindan-1-one (7.5 g) in toluene (50 ml) was added and the mixture heated under reflux for 10 hours. The reaction mixture was worked-up in standard fashion and the excess diethyl malonate removed in vacuo. The residue was heated under reflux with acetic acid (150 ml), conc. hydrochloric acid (150 ml) and water (60 ml). After standard work-up 2-(5-bromo-1-oxo-indan-2-yl) acetic acid was obtained.

The above acid (4.4 g) was treated with zinc, mercuric chloride and hydrochloric acid as in example 2 to give 2-(5-bromoindan-2-yl) acetic acid (4.2 g).

The above acid (4.2 g) was added to a suspension of sodium borohydride (0.75 g) in tetrahydrofuran (20 ml) at −5°. After 2 hours boron trifluoride etherate (3.5 g) was added and the mixture stirred for 16 hours at room temperature. The reaction was quenched with water and worked-up in standard fashion to give a crude product which was purified by column chromatography (silica; 1:1, ether: hexane) to give 2-(5-bromoindan-2-yl) ethanol (2 g).

The above alcohol was oxidised under Swern conditions to 2-(5-bromoindan-2-yl)ethanal and thence to the title compound by analogy with example 1.

EXAMPLE 7

(2Z,4E)N-Isobutyl 2-fluoro-3-methyl-6-(5-bromo-6-fluoroindan-2-yl hexa-2,4-dienamide 3-Fluoro-4-bromotoluene (ex. Fluorochem) (24.9 g) in tetrachloromethane was reacted with N-bromosuccinimide (23.5 g) in the presence of benzoyl peroxide and light to give 3-fluoro-4-bromobenzyl bromide (30 g). The bromide was treated with sodium and diethyl malonate as in example 6, subsequent acid hydrolysis afforded 3-(3-fluoro-4-bromophenyl) propanoic acid (10 g).

The above acid was subjected to cyclisation with polyphosphoric acid, to give 5-fluoro-6-bromoindan- 1-one and thence converted to 2-allyl-5-fluoro-6-bromoindan-1-one by analogy with example 2.

The above compound (1.15 g) in triethylsilane (1.5 ml) was treated over 10 minutes at 0° with trifluoroacetic acid (1.65 ml). The mixture was stirred at room-temperature overnight, diluted with water and worked-up in conventional fashion. Purification by column chromatography (silica; hexane) gave 2-allyl-5-fluoro-6-bromoindane (0.3 g). The latter was subjected to ozonolysis to give 2-(5-fluoro-6-bromoindan-2-yl)-ethanal by analogy with example 2.

The above aldehyde was converted to the title compound by analogy with example 1.

EXAMPLE 8

(2E,4Z)N-Isobutyl 4-fluoro-11-(3,5-bistrifluoromethylbenzyloxy)undeca-2,4-dienamide (i) Chloroacetyl chloride (ex. Aldrich) (50 g) was added dropwise, with stirring, to isobutylamine (ex. Aldrich) (70 ml) in dry ether (250 ml) at 0° C. When the mixture had reached room temperature it was worked up in conventional fashion to give N-isobutyl 2-chloroacetamide. The latter (20 g) was heated for 3 hours at 120° C. with triethylphosphite (23 g). The mixture was subjected to distillation in vacuo to give N-isobutyl diethylphosphono acetamide (22.5 g, bp. 140°-142.5° C. at 0.1 mm).

(ii) Diethyl oxalate (415 μl) (ex. Aldrich) and ethyl fluoroacetate (269 μl) (ex. Fluorochem) were added to hexane-washed sodium hydride (112 mg at 60°) in anhydrous tetrahydrofuran (15 ml). After heating under reflux for 3 hours, the mixture was allowed to cool to room temperature and 7-(3,5-bistrifluoromethylbenzyloxy)heptan-1-al (3.47 mmol) (prepared according to methods described in EP-A-164187) in dry THF (3 ml) was added. After 18 hours at room temperature, the reaction was worked up in conventional manner and the crude product purified by column chromatography (Silica; 4:1, hexane:ether) to give 2-fluoro-9-(bistrifluoromethylbenzyloxy)non-2-enoate as a colourless oil (0.9 g).

(iii) The above ester (0.87 g) in dry dichloromethane (8 ml) was treated with diisobutylaluminium hydride in toluene (1M, 3.92 ml) at −20° C. The reaction mixture was allowed to reach 0° C. over 2 hours and treated sequentially with saturated ammonium chloride and 2N hydrochloric acid. After conventional work-up the crude product was purified by column chromatography (silica; 80:20, ether:hexane) to give (Z)-2-fluoro-9-(bis-trifluoromethyl-benzyloxy)non-2-ene-1-ol as a colourless oil (0.7 g).

Dimethyl sulphoxide (293 mg) in dry dichloromethane (3 ml) was added to oxalyl chloride (162 mg) in dichloromethane (14 ml) at −60° C. After 10 minutes the above alcohol (0.73 g) in dichloromethane (3 ml) was added and the mixture kept at −60° C. for 1 hour. Triethylamine (1.01 ml) was added and the whole allowed to reach 0° C. gradually. Conventional work-up gave (Z)-2-fluoro-9-(bistrifluoromethylbenzyloxy)non-2-ene-1-al.

(iv) Lithium diisopropylamide in dry tetrahydrofuran (10 ml) was prepared at −10° C. from n-butyl lithium in hexane (1.6M, 2.27 ml) and diisopropylamine (532 μl). N-isobutyl diethylphosphonoacetamide (0.456 g) in dry THF (3 ml) was added at −78° C. and the mixture held at −60° to −65° C. for 2 hours. The above aldehyde (1.816 mmol) in dry THF (3 ml) was added at −65° C. and the orange solution kept at −5° C. for 16 hours. After dilution with diethyl ether and washing with water the reaction mixture was worked up in standard fashion and the crude product purified by column chromatography (silica; ether:hexane, 40:60) to give colourless needless (0.45 g) of the title compound.

Characterising data for compounds of formula 1

The stereochemistry of the examples is as described previously. Where mixtures are obtained the compound comprises >85% of the stated isomer.

Nuclear magnetic resonance data and physiochemical data of compounds are given in Tables 2 and 3.

TABLE 1

$Q^1Q(CH=CH)_a(CR^4=CF)(CR^5=CR^6)_bC(=O)NHR^1$

| Example No. | $Q^1$ and link position | Substituent on $Q^1$ | Q | $R^4$ | $R^5$ | $R^6$ | a | b | $R^1$ |
|---|---|---|---|---|---|---|---|---|---|
| 1 | ph | 3,5-$(CF_3)_2$ | $CH_2O(CH_2)_6$ | $CH_3$ | — | — | 1 | 0 | i-Bu |
| 2 | 2-in | 4-Cl | $CH_2$ | $CH_3$ | — | — | 1 | 0 | i-Bu |
| 3 | 2-na | — | $O(CH_2)_7$ | $CH_3$ | — | — | 1 | 0 | i-Bu |
| 4 | ph | 3,5-$(CF_3)_2$ | $O(CH_2)_7$ | $CH_3$ | — | — | 1 | 0 | i-Bu |
| 5 | ph | 3,4-$Cl_2$ | $O(CH_2)_7$ | $CH_3$ | — | — | 1 | 0 | i-Bu |
| 6 | 2-in | 5-Br | $CH_2$ | $CH_3$ | — | — | 1 | 0 | i-Bu |
| 7 | 2-in | 5-Br,6-F | $CH_2$ | $CH_3$ | — | — | 1 | 0 | i-Bu |
| 8 | ph | 3,5-$(CF_3)_2$ | $CH_2O(CH_2)_6$ | H | H | H | 0 | 1 | i-Bu |

Key:
ph = phenyl
in = indanyl
na = naphthyl

TABLE 2

| | Nuclear Magnetic Resonance Data |
|---|---|
| Compound No. | Details of spectrum |
| 1 | 7.81(s, 3H); 6.57(d, 1H); 6.37(1H); 6.09, 6.03(2t, 1H); 4.61(s, 2H); 3.55(t, 2H); 3.19(t, 2H); 2.27(d, 3H); 2.22(m, 2H); 1.86, 1.69, 1.40(3m, 9H); 0.95(d, 6H) |
| 2 | 7.10(m, 3H); 6.63(d, 1H); 6.38(s, 1H); 6.10, 6.03(2t, 1H); 3.20(t, 2H); 3.11, 2.68, 2.42(3m, 5H); 2.30(d, 3H); 1.86(m, 1H); 0.69(d, 6H) |
| 3 | 7.76(m, 2H); 7.44(t, 1H); 7.33(t, 1H); 7.18(m, 1H); 7.12(s, 1H); 6.56(d, 1H); 6.35(1H); 6.09, 6.04(2t, 1H); 4.08(t, 2H); 3.18(t, 2H); 2.31(d, 3H); 2.24(m, 2H); 1.87, 1.45(m's, 11H); 0.96(d, 6H) |
| 4 | 7.42(s, 1H); 7.28(s, 2H); 6.55(d, 1H); 6.36(1H); 6.07, 6.02(2t, 1H); 3.98(t, 2H); 3.17(t, 2H); 2.27(d, 3H); 2.21(m, 2H); 1.82, 1.42(m's, 11H); 0.92(6H, d) |
| 5 | 7.27(d, 1H); 6.97(s, 1H); 6.73(d, 1H); 6.54(d, 1H); 6.35(1H); 6.07, 5.99(2t, 1H); 3.88(t, 2H) |

TABLE 2-continued

Nuclear Magnetic Resonance Data

| Compound No. | Details of spectrum |
|---|---|
|  | 3.15(t, 2H); 2.28(d, 3H); 2.18(m, 2H); 1.78, 1.38(m's, 11H); 0.93(6H, d) |
| 6 | 7.31(d, 1H); 7.29(s, 1H); 7.08(d, 1H); 6.60(d, 1H); 6.36(1H); 6.08, 6.02(2t, 1H); 3.19(m, 2H); 3.07, 2.63, 2.39(3m, 5H); 2.29(d, 3H); 1.78(m, 1H); 0.93(d, 6H) |
| 7 | 7.32(d, 1H); 6.95(d, 1H); 6.59(d, 1H); 6.37(1H); 6.05, 6.00(2t, 1H); 3.15(t, 2H); 2.99, 2.59, 2.39(3m, 5H); 2.29(d, 3H); 1.80(m, 1H); 0.93(d, 6H) |
| 8 | 7.80(s, 3H); 6.98(2d, 1H); 6.00(d, 1H); 5.13(2t, 1H); 5.62(1H); 4.58(s, 2H); 3.40(t, 2H); 3.16(t, 2H); 2.21(m, 2H); 1.83(m, 1H); 1.66, 1.40(2m, 8H); 0.90(d, 6H) |

TABLE 3

| Example No. | Physicochemical data chromatography | | mp (°C.) |
|---|---|---|---|
|  | $R_f$ | solvent system |  |
| 1. | 0.57 | B |  |
| 2. | 0.65 | A |  |
| 3. | 0.40 | D | 56° |
| 4. | 0.68 | B |  |
| 5. | 0.48 | B |  |
| 6. | 0.20 | E | 79° |
| 7. | 0.64 | A | 72-6° |
| 8. | 0.62 | A | 94° |

A: Diethyl ether
B: Diethyl ether/hexane (50:50)
C: Diethyl ether/hexane (60:40)
D: Diethyl ether/hexane (30:70)
E: Diethyl ether/hexane (20:80)

| Formulations | |
|---|---|
| 1. Emulsifiable Concentrate | |
| Compound of formula (I) | 10.00 |
| Ethylan KEO | 20.00 |
| Xylene | 67.50 |
| Butylated Hydroxyanisole | 2.50 |
|  | 100.00 |
| 2. Wettable Powder | |
| Compound of formula (I) | 25.00 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
|  | 100.00 |
| 3. Dust | |
| Compound of formula (I) | 0.50 |
| Butylated Hydroxyanisole | 0.10 |
| Talc | 99.40 |
|  | 100.00 |
| 4. Bait | |
| Compound of formula (I) | 40.25 |
| Icing Sugar | 59.65 |
| Butylated hydroxy toluene | 0.10 |
|  | 100.00 |
| 5. Lacquer | |
| Compound of formula (I) | 2.50 |
| Resin | 5.00 |
| Butylated Hydroxyanisole | 0.50 |
| High aromatic white spirit | 92.00 |
|  | 100.00 |
| 6. Aerosol | |
| Compound of formula (I) | 0.30 |
| Butylated Hydroxy anisole | 0.10 |
| 1,1,1-Trichloroethane | 4.00 |
| Odourless Kerosene | 15.60 |
| Arcton 11/12, 50:50 mix | 80.00 |
|  | 100.00 |
| 7. Spray | |
| Compound of formula (I) | 0.1 |
| Butylated Hydroxyanisole | 0.1 |
| Xylene | 10.0 |
| Odourless Kerosene | 89.8 |
|  | 100.00 |
| 8. Potentiated Spray | |
| Compound of formula (I) | 0.1 |
| Piperonyl Butoxide | 0.5 |
| Butylated Hydroxyanisole | 0.1 |
| Xylene | 10.1 |
| Odourless Kerosene | 89.2 |
|  | 100.00 |

BIOLOGICAL ACTIVITY

The following examples illustrate, in a non-limiting manner, the pesticidal activity of compounds of formula (I):

EXAMPLE A

Spray Tests

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

*Musca domestica*

20 female Musca were contained in a cardboard cylinder with gauze over both ends. Solution containing the compound was sprayed onto the insects so enclosed and mortality assessed after 48 hours at 25° C.

The following compounds were active at up to 1000 ppm:
1,2,3,5

The following compounds were active at up to 200 ppm:
4,7,8

*Sitophilus granarius*

20 adult Sitophilus were added to 10 g wheat which had been previously treated with 2 ml of the solution containing the compound. Mortality was assessed after 6 days at 25° C.

The following compounds were active at up to 1000 ppm:
1,2

*Tribolium castaneum*

20 adult Tribolium were added to 10 g wheat which had been previously treated with 10 ml of the solution containing the compound. Mortality was assessed after 6 days at 25° C.

The following compounds were active at up to 1000 ppm:
1,2

Plutella xylostella

7 Plutella larvae (3rd instar) were sprayed with solution containing the compound and added to a Chinese cabbage leaf which had been similarly sprayed and left to dry. Mortality was assessed after 2 days at 25° C.

The following compounds were active at up to 200 ppm:
1,4,5,7,8

The following compounds were active at up to 40 ppm:
2

Tetranychus urticae

Leaf discs of infested french bean were sprayed with the solution containing the compound. Mortality was assessed after 2 days at 25° C.

The following compounds were active at up to 1000 ppm:
1,2,3,4,5,6,7,8

Spodoptera littoralis

Uninfested leaves were sprayed with the test solution containing the compound (+pip but) and left to dry. These were then infested with 10 newly hatched larvae. Mortality was assessed after 3 days.

The following compounds were active at up to 1000 ppm:
2,3,4,8

The following compounds were active at 200 ppm:
5,6

Diabrotica undecimpunctata

2nd instar larvae and their food were sprayed on filter paper with the solution containing the compound. Activity was assessed at 2 days.

The following compounds were active at up to 1000 ppm:
1,4,5,6

EXAMPLE B

Topical Application Tests

Blatella germanica

The following compounds were active at up to 10 μg per insect (+piperonyl butoxide):
2,3,5,7

Spodoptera littoralis 0.5 μl of a solution of the compound under test (with or without 50 μg pip but) in acetone was used for topical application to 3rd instar larvae. Mortality was assessed after 48 hours.

The following compounds were active at up to 10 μg per larva (+50 μg piperonyl butoxide):
1,2,3,6,7,8

Comparative Tests

Spray Tests

Activity of analogues of compounds of the formula (I) but wherein the 2-substituent is other than fluorine, disclosed in EP 251472 was compared in the above tests.

Sitophilus granarius

Analogue of compound 1 (EP 251472) had an lc50 of >200 ppm.

Compound 1 had an lc50 of 130 ppm.

I claim:

1. A compound of the formula (I):

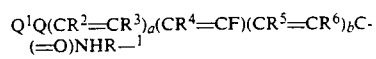

or a salt thereof, wherein $Q^1$ is a phenyl ring or a fused bicyclic ring system containing 9 of 10 ring carbon atoms, at least one ring being aromatic, or a phenyl ring or fused bicyclic ring system containing 9 or 10 ring carbon atoms substituted with halo, cyano, $C_{1-6}$ alkyl and $C_{1-6}$ alkoxy each optionally substituted by one or more halogen atoms or the substituent is a group $S(O)_m R^9$ wherein m is 0, 1 of 2 and $R^9$ is $C_{1-6}$ alkyl optionally substituted by halo, or $Q^1$ is a diahalovinyl group; Q is an alkyl chain containing 1 to 12 carbon atoms and optionally containing one or two oxygen atoms and/or an unsaturated group $-CR^7=CR^8-$, or $-\equiv C-$, wherein $R^7$ and $R^8$ are selected from hydrogen or halo; a is 0 or 1, b is 0 or 1; the sum of a and b is 0 or 1; $R^2$, $R^3$, $R^4$, $R^5$ and $R^6$ are the same or different, and are independently selected from hydrogen, halo and $C_1$-$C_4$ alkyl; and $R^1$ is selected from hydrogen and $C_{1-6}$ hydrocarbyl optionally substituted by dioxalanyl, halo, cyano, trifluoromethyl, trifluoromethylthio or $C_{1-6}$ alkoxy.

2. A compound according to claim 1 wherein the ring system $Q^1$ is selected from phenyl, indanyl, naphthyl and tetrahydronaphthyl.

3. A compound according to claim 1 wherein Q is a $CH_2O(CH_2)_6$, $CH_2$, $O(CH_2)_7$ or $O(CH_2)_9$ group, the oxygen atom being adjacent to $Q^1$.

4. A compound according to claim 1 wherein $R^2$, $R^3$ are hydrogen, $R^4$ and $R^5$ are chosen from hydrogen and methyl and $R^6$ is chosen from hydrogen and fluoro.

5. A compound of the formula (IA)

wherein $Q^1$, Q and $R^1$ are as hereinbefore defined.

6. A compound of the formula (IB)

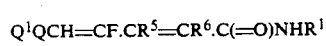

wherein $R^5$ is hydrogen or methyl, $R^6$ is hydrogen or fluoro and $Q^1$, Q and $R^1$ are as hereinbefore defined.

7. A compound selected from:
(2Z,4E)N-isobutyl-2-fluoro-3-methyl-11-(3,5-bistrifluoromethylbenzyloxy)-undeca-2,4-dienamide,
(2Z,4E)N-isobutyl-2-fluoro-3-methyl-6-(4-chloro-2-indanyl)hexa-2,4-dienamide.

8. A method for the control of arthropod or helminth pests which comprises administering to the arthropod or helminth or their environment an effective amount of a compound of the formula (I) as defined according to claim 1.

9. A method for the control of pesticidal infestation on plants which comprises administering an effective amount of a compound of the formula (I) as defined according to claim 1 to the plant susceptible to pest infestation.

10. A method for the control of pesticidal infestation on stored products which comprises administering an effective amount of a compound of formula (I) as defined according to claim 1 to the stored product susceptible to pest infestation.

11. A method for the control of pesticidal infestation on an environment which comprises administering an effective amount of a compound of formula (I) as defined according to claim 1 on an environment susceptible to pest infestation.

12. A method for the control of pesticidal infestation on animals which comprises administering to the animal an effective amount of a compound of the formula (I) as defined according to claim 1.

13. The compound of claim 1 in which $R^7$ and $R^8$ are fluoro.

14. A pesticidal composition consisting essentially of a compound as defined in claim 1 in admixture with a carrier or diluent.

15. The pesticidal composition of claim 14 further including piperonyl butoxide (PB) or butylated hydroxy anisole.

* * * * *